(12) United States Patent
Mestl et al.

(10) Patent No.: US 11,014,075 B2
(45) Date of Patent: May 25, 2021

(54) SYNTHESIS OF A MOVNBTE CATALYST FROM LOW-COST METAL OXIDES

(71) Applicant: Clariant Produkte (Deutschland) GmbH, Frankfurt am Main (DE)

(72) Inventors: Gerhard Mestl, Munich (DE); Klaus Wanninger, Kolbermoor (DE); Daniel Melzer, Munich (DE); Maria Cruz Sanchez-Sanchez, Munich (DE); Julia Tseglakova, Muehlheim an der Ruhr (DE); Johannes Lercher, Ottobrunn (DE)

(73) Assignee: Clariant Produkte Gmbh, Frankfurt am Main (DE)

( * ) Notice: Subject to any disclaimer, the term of this patent is extended or adjusted under 35 U.S.C. 154(b) by 0 days.

(21) Appl. No.: 16/481,210

(22) PCT Filed: Jan. 26, 2018

(86) PCT No.: PCT/EP2018/052013
§ 371 (c)(1),
(2) Date: Jul. 26, 2019

(87) PCT Pub. No.: WO2018/141654
PCT Pub. Date: Aug. 9, 2018

(65) Prior Publication Data
US 2020/0290026 A1 Sep. 17, 2020

(30) Foreign Application Priority Data
Jan. 31, 2017 (DE) .......................... 102017000861.2

(51) Int. Cl.
*B01J 27/057* (2006.01)
*B01J 35/02* (2006.01)
(Continued)

(52) U.S. Cl.
CPC ......... *B01J 27/0576* (2013.01); *B01J 35/026* (2013.01); *B01J 37/0236* (2013.01);
(Continued)

(58) Field of Classification Search
CPC . B01J 23/22; B01J 23/002; B01J 23/28; B01J 27/00576; B01J 31/04;
(Continued)

(56) References Cited

U.S. PATENT DOCUMENTS 5,281,745 A 1/1994 Ushikubo
5,380,933 A 1/1995 Ushikubo
(Continued)

FOREIGN PATENT DOCUMENTS

DE 10119933 A1 10/2002
EP 0318295 5/1989
(Continued)

OTHER PUBLICATIONS

Desanto, Peter, Structural aspects of the M1 and M2 phases . . . Z. Kristallogr. 219 (2004) 152-165.
(Continued)

*Primary Examiner* — Patricia L. Hailey (57) ABSTRACT

A novel catalyst and process for producing a mixed oxide material containing molybdenum, vanadium, tellurium and niobium is disclosed. The material can be used as a catalyst for the oxidative dehydrogenation of ethane to ethene or the oxidation of propane to acrylic acid.

20 Claims, 7 Drawing Sheets

X-ray powder diffraction pattern of the MoVTeNb mixed oxide of example (51) Int. Cl.
*B01J 37/02* (2006.01)
*B01J 37/03* (2006.01)
*B01J 37/04* (2006.01)
*C01B 19/00* (2006.01)
*C07C 5/333* (2006.01)

(52) U.S. Cl.
CPC ............ B01J 37/038 (2013.01); B01J 37/04 (2013.01); C01B 19/002 (2013.01); C07C 5/3332 (2013.01); *C01P 2002/50* (2013.01); *C01P 2002/72* (2013.01); *C01P 2004/61* (2013.01); *C07C 2523/20* (2013.01); *C07C 2523/22* (2013.01); *C07C 2523/28* (2013.01); *C07C 2527/057* (2013.01)

(58) Field of Classification Search
CPC .. B01J 31/2204; B01J 31/2226; B01J 35/002; B01J 37/08; B01J 2523/55; B01J 2523/56; B01J 2523/64; B01J 2523/68; B01J 27/0576; C07C 5/3322; C07C 5/48; C07C 253/24; C07C 255/08; C07C 2523/20; C07C 2523/22; C07C 2523/28; C07C 2527/057; C01P 2002/72; C01P 2004/61
USPC ......... 502/215, 311, 312; 585/654; 562/542, 562/546, 547, 549
See application file for complete search history.

(56) References Cited

U.S. PATENT DOCUMENTS

| | | | | |
|---|---|---|---|---|
| 5,422,328 | A * | 6/1995 | Ushikubo | B01J 23/28 502/309 |
| 5,616,815 | A * | 4/1997 | Atkins | B01J 27/188 568/700 |
| 6,867,328 | B2 | 3/2005 | Borgmeier | |
| 7,009,075 | B2 | 3/2006 | Hazin | |
| 7,038,082 | B2 | 5/2006 | Borgmeier | |
| 7,375,052 | B2 * | 5/2008 | Tu | B01J 23/002 502/305 |
| 7,473,666 | B2 * | 1/2009 | Yanagi | B01J 23/002 502/233 |
| 9,073,036 | B2 | 7/2015 | Hagemeyer | |
| 2003/0088118 | A1 * | 5/2003 | Komada | C07C 253/24 558/332 |
| 2003/0187299 | A1 * | 10/2003 | Machhammer | C07C 51/252 562/547 |
| 2004/0063990 | A1 * | 4/2004 | Gaffney | C07C 51/215 558/322 |
| 2004/0082190 | A1 * | 4/2004 | Borgmeier | B01J 27/0576 438/722 |
| 2008/0200716 | A1 * | 8/2008 | Lugmair | B01J 27/0576 558/319 |
| 2010/0255985 | A1 * | 10/2010 | Gaffney | C07C 5/48 502/312 |
| 2010/0255986 | A1 * | 10/2010 | Gaffney | B01J 37/0036 502/312 |
| 2010/0256432 | A1 * | 10/2010 | Arnold | C07C 5/48 585/655 |
| 2015/0119622 | A1 * | 4/2015 | De Rooij | B01J 23/002 585/658 |
| 2016/0038922 | A1 * | 2/2016 | De Rooij | B01J 37/08 585/658 |
| 2019/0240647 | A1 * | 8/2019 | Gao | B01J 23/22 |
| 2019/0366311 | A1 * | 12/2019 | Mestl | B01J 37/036 |
| 2020/0061583 | A1 * | 2/2020 | Mestl | B01J 37/033 |
| 2020/0139349 | A1 * | 5/2020 | Mestl | B01J 23/28 |
| 2020/0215516 | A1 * | 7/2020 | Mestl | B01J 35/1019 |
| 2020/0290026 | A1 * | 9/2020 | Mestl | B01J 37/04 |

FOREIGN PATENT DOCUMENTS

| | | | | |
|---|---|---|---|---|
| JP | H06227819 | | 8/1994 | |
| JP | 07232071 | | 9/1995 | |
| JP | 08226796 | | 9/1996 | |
| JP | 2004313956 | | 11/2004 | |
| WO | WO-2008152952 A1 * | 12/2008 | .......... B01J 23/8885 |
| WO | 2009106474 | | 9/2009 | |

OTHER PUBLICATIONS

Valente, Jamie S., Chemical, Structural, and Morphological Changes of a MoVTeNb catalyst . . . ACS Catal. 4, (2014) 1292-1301.
Sanfiz, A. Celaya, Preparation of Phase-Pure M1 MoVTeNb Oxide . . . Top. Catal. 50, (2008) 9-32.
Ushikubo, Takashi Ammoxidation of propane over Mo—V—Nb—Te mixed oxide catalysts, Studies in Surface Science and Catalysis 112 (1997) 473-480.
P. Botella, Solid State Science 7 (2005) 507-519.

* cited by examiner

Figure 1: X-ray powder diffraction pattern of the MoVTeNb mixed oxide of example Figure 2: X-ray diffraction pattern of the MoVTeNb mixed oxide of example 2

Figure 3: X-ray diffraction pattern of the MoVTeNb mixed oxide of comparative example 2

Figure 4: Pore distribution of the MoVTeNb mixed oxide of example 1

Figure 5: Pore distribution of the MoVTeNb mixed oxide of example 2

Figure 6: Pore distribution of the MoVTeNb mixed oxide of comparative example 1

Figure 7: Comparison of the catalytic activity

SYNTHESIS OF A MOVNBTE CATALYST FROM LOW-COST METAL OXIDES

The invention relates to a novel process for producing a mixed oxide material containing molybdenum, vanadium, tellurium and niobium as catalyst for the oxidative dehydrogenation of ethane to ethene or the oxidation of propane to acrylic acid and a process for producing the mixed oxide material.

MoVNbTe mixed oxides for the oxidation of propane to acrylic acid or for the oxidative dehydrogenation of ethane to ethene are prior art. More than 200 patents and numerous scientific publications are concerned with catalysts based on MoVNbTe mixed oxides. The promotion of these mixed oxides with other metals of the Periodic Table is known. Here, the highest previously described acrylic acid yields are 60% and those of ethene are about 80%.

The MoVNbTe basis system based on four elements for a catalyst has been proposed by Mitsubishi for the ammoxidation of propane to acrylonitrile (1989, EP 318295 A1) and the oxidation to acrylic acid (1994, EP 6088038 A2). JP H07-053414 (Mitsubishi) discloses a catalytic process for preparing ethylene by oxidative hydrogenation of ethane at low temperature, in high yield and with high selectivity. This process for preparing ethylene comprises contacting ethane with a gas containing molecular oxygen in the presence of a catalyst composition at elevated temperature, where the catalyst composition contains a mixed metal oxide which has molybdenum, vanadium, tellurium and oxygen as main components and displays an X-ray powder diffraction pattern which has essentially the following relative peak intensities: 2θ (+−0.4°), rel. int.: 22.1° (100), 28.2° (400~3), 36.2° (80~3), 45.1° (40~3), 50° (50~3).

MoVNbTe catalysts consist mainly of two orthorhombic phases which are referred to as "M1" and "M2" (T. Ushikubo, K. Oshima, A. Kayou, M. Hatano, Studies in Surface Science and Catalysis 112, (1997), 473). The M1 phase appears to play the important role in the selective oxidation reactions.

According to P. De Santo et al., Z. Kristallogr. 219 (2004) 152, the main phases M1 and M2 in multimetal oxide catalysts for the selective oxidation can be described for example, by the following structural formulae:

$Mo_1V_{0.15}Te_{0.12}Nb_{0.128}O_{3.7}$ or
$Mo_{7.8}V_{1.2}Te_{0.937}Nb_1O_{28.9}$  M1:

*$Mo_1V_{0.32}Te_{0.42}Nb_{0.08}O_{4.6}$ or
$Mo_{4.31}V_{1.36}Te_{1.81}Nb_{0.33}O_{19.81}$  M2:

The two main phases can also occur with a somewhat different stoichiometry. Thus, both vanadium and molybdenum are present in the center of an octahedron of oxygen atoms and are therefore partly exchangeable in the structure, so that the same structure, e.g. the M1 phase, is also possible with a higher vanadium content. A detailed study of these relationships may be found in P. Botella et al., Solid State Science 7 (2005) 507-519. The M2 phase in particular is not active for oxidative dehydrogenation of ethane. (See J. S. Valente et al., ACS Catal. 4(2014), 1292-1301, especially p. 1293). A catalyst consisting of very pure M1 phase is therefore desirable for the oxidative dehydrogenation of ethane. Attempts are therefore also made to produce these crystal phases cleanly and separately.

EP 529853 A2 discloses a catalyst which is suitable for preparing a nitrile from an alkane, wherein the catalyst has the empirical formula $MoV_bTe_cX_xO_n$, where X is at least one of Nb, Ta, W, Ti, Al, Zr, Cr, Mn, Fe, Ru, Co, Rh, Ni, Pd, Pt, Sb, Bi, B and Ce, b is from 0.01 to 1.0, c is from 0.01 to 1.0; x is from 0.01 to 1.0 and n is a number by means of which the total valence of the metallic elements is satisfied and the catalyst has X-ray diffraction peaks at the following 2θ angles in its X-ray diffraction pattern: diffraction angle at 2θ (22.1°+/−0.3°, 28.2°+/−0.3°, 36.2°+/−0.3°, 45.2°+/−0.3°, 50.0°+/−0.3').

JP H07-232071 discloses a catalytic process for preparing a nitrile at a relatively low temperature and in a high yield, using an alkane as raw material and a particular catalyst. The main component of the catalyst is a mixed metal oxide composed of molybdenum, vanadium, tellurium, oxygen and X (X is one or more elements selected from the group consisting of niobium, tantalum, etc.), where the ratio of the main components, i.e. with the exception of oxygen, is expressed by the formulae I to IV: I) 0.25<rMo<0.98, II) 0.003<rV<0.50, III) 0.003<rTe<0.50, IV) 0≤rX<0.5, (rMo, rV, rTe and rX are in each case the molar parts of molybdenum, vanadium, tellurium and X) and in the XRD displays XRD bands of this mixed oxide at the various 2θ angles 9.0°±0.3°, 22.1°±0.3°, 27.3°±0.3°, 29.2°±0.3° and 35.4°±0.3°. According to this document, a nitrile can be prepared in high yield at low temperature by reacting an alkane without the presence of a halogenated substance, e.g. with water, etc., in the reaction system.

Other successful attempts to produce a pure M1 phase are based on dissolving the M2 phase out from the phase mixture. These experiments are described, for example, in EP 1301457 A2, EP 1558569 A1 or WO 2009106474 A2.

A. C. Sanfiz et al., Top. Catal. 50 (2008) 19-32, describe hydrothermal syntheses of MoVNbTe oxide. The syntheses start out exclusively from soluble compounds.

Telluric acid $Te(OH)_6$ is generally used as soluble compound of tellurium. In the most readily available oxidic tellurium compound $TeO_2$, tellurium has the oxidation state +4. Unfortunately, tellurium dioxide ($TeO_2$) is sparingly soluble in water. Furthermore, the tellurium in telluric acid has the oxidation state +6. Tellurium therefore has to be oxidized up in the preparation of telluric acid. The most widespread synthesis is carried out by oxidation of tellurium oxide with hydrogen peroxide, which on a large scale is accompanied by safety problems because hydrogen peroxide can disproportionate into water and oxygen in a spontaneous decomposition. For this reason, telluric acid can be prepared in large amounts only with difficulty.

A synthesis of the MoVNbTe mixed oxide without use of telluric acid therefore has the potential for being significantly cheaper.

The Nb component used in the synthesis of MoVNbTe mixed oxides is generally ammonium niobium oxalate. Niobium oxide, on the other hand, is sparingly soluble and therefore has only limited suitability as starting compound.

Watanabe (Applied Catal. A General, 194-195 (2000) 479-485) describes, inter alia, the hydrothermal synthesis from the sparingly soluble precursors $MoO_3$, $V_2O_5$ and $TeO_2$. The hydrothermal synthesis gives a precursor for an ammoxidation catalyst which compared to a catalyst produced by the known dry method has twice the activity after calcination. The mixed oxides produced by a solid-state reaction display a rather low activity. It has been proposed that the higher activity of the catalyst produced by the hydrothermal synthesis is due first and foremost to the higher surface area.

It is an object of the present invention to provide a mixed oxide material containing molybdenum, vanadium, tellurium and niobium ("MoVTeNb mixed oxide") which has a high content of M1 phase and as catalyst material, especially for the oxidation of ethane to ethylene, displays a very high activity and selectivity.

This object is achieved by a process for producing a mixed oxide material, comprising the steps:

a) production of a mixture of starting compounds, which contains starting compounds containing molybdenum, vanadium, niobium and tellurium and also two chelating oxo ligands, b) hydrothermal treatment of the mixture of starting compounds at a temperature of from 100° C. to 300° C. to give a product suspension, c) isolation and drying of the solid present in the product suspension resulting from step b), d) activation of the solid obtained from step c) in an inert gas.

The mixture of starting compounds is preferably present as aqueous suspension and is subsequently hydrothermally treated. The term "hydrothermally" refers predominantly to reaction conditions for producing a catalyst material in the presence of water and at elevated temperature and/or elevated pressure, for example in an autoclave. Here, the pressure can be in the range from 5 to 30 bar, preferably from 10 to 27 bar. Illustrative pressure ranges are from 11 to 20 bar.

As a result of the hydrothermal treatment (step b)), a product suspension containing the MoVNbTe mixed oxide as solid is obtained. In the process of the invention the isolation of the solid of the suspension in step c) can be carried out by means of one or more filtration steps, e.g. filtering-off of the mother liquor. Drying can be carried out in a single step or in two steps in flowing or static air. The first drying step is preferably carried out at from 60° C. to 150° C. (particularly preferably from 80° C. to 120° C.), and the second drying step can be carried out at from 200° C. to 350° C. (particularly preferably from 220° C. to 280° C.). In addition, step c) of the process of the invention can comprise one or more washing steps, calcination steps (thermal treatment) and/or milling steps. The calcination can be carried out from 200 to 500° C., preferably from 250° C. to 350° C., in air.

After drying of the filtrate in step c), the dried mixture can optionally be activated, e.g. in a flowing or static inert gas atmosphere at from about 500° C. to 700° C. for at least 1 hour (step d)). A suitable inert gas is, in particular, nitrogen, helium or argon. Preference is given to carrying out activation in the range from 550° C. to 650° C. For example, activation can be carried out at about 600° C. for about 2 hours.

The starting compounds are the molybdenum-, vanadium-, tellurium- and niobium-containing starting materials of the hydrothermal synthesis (precursor compounds). These each contain one or more of the elements molybdenum, vanadium, tellurium or niobium.

The molybdenum-containing starting compound can, for example, be an ammonium heptamolybdate or molybdenum trioxide, the vanadium-containing starting compound can, for example, be an ammonium metavanadate, vanadyl sulfate or vanadium pentoxide, the niobium-containing starting compound can, for example, be ammonium niobium oxalate or niobium oxalate or niobium oxide. The tellurium-containing starting compound according to the invention is preferably tellurium dioxide.

The tellurium-containing starting compound can be one in which the tellurium is in the oxidation state +6 or +4, i.e. as tellurium(IV) or tellurium(VI) cation. Particular preference is given to telluric acid, tellurium dioxide or a compound of the formula $M_x^{n+}TeO_3$ (where n=1 or 2 and x=2/n), where M is an alkali metal or alkaline earth metal, e.g. $Na_2TeO_3$. The tellurium-containing starting compound is particularly preferably tellurium dioxide which can be present in any degree of hydration. If tellurium dioxide is used as starting compound, the tellurium dioxide has a particle size having a $D_{90}$ of <100 μm. It is particularly preferred that the $D_{50}$ value for the tellurium dioxide used as starting compound is less than 35 μm.

In addition, the niobium-containing starting compound, which is preferably niobium oxide, can likewise have a particle size having a $D_{90}$ of <100 μm, preferably $D_{90}$<75 μm, particularly preferably $D_{90}$<50 μm. The niobium-containing starting compound used, which is preferably niobium oxide, can optionally have a particle size $D_{50}$ of <50 μm or <35 μm.

In addition, all starting compounds used can have a particle size having a $D_{90}$ of <100 μm, preferably $D_{90}$<75 μm, particularly preferably $D_{90}$<50 μm. The starting compounds can optionally have a particle size $D_{90}$ of <50 μm or <35 μm.

The starting compounds used, i.e., for example, metal oxides such as tellurium dioxide, are present as powder and have a particle size distribution. The particle size $D_{90}$ is defined as the limit of the particle diameter in the particle size distribution under which 90% of all particles lie. The particle size of the meridian, i.e. the particle size below which half of all particles in the particle size distribution lie, is also referred to as particle size $D_{50}$. The particle size $D_{50}$ of the tellurium dioxide used as starting compound is particularly preferably less than 35 μm.

The desired particle size $D_{90}$ or $D_{50}$ of the starting compound can be obtained by starting from a powder having a coarser particle size distribution and mechanically comminuting the particles. This can be carried out by milling, with all suitable means with which a person skilled in the art is familiar, e.g. impact mills, planetary mills, mortars, etc., being able to be used.

An advantage of the production process of the invention is that a synthesis of the M1 phase from insoluble and inexpensive oxides is possible, e.g. $MoO_3$, $V_2O_5$, $Nb_2O_5$ and $TeO_2$ are used as starting compounds. Citric acid, glycol and oxalic acid, in particular, have been found to be suitable chelating oxo ligands.

The two chelating oxo ligands should preferably each be present in an Mo/oxo ligand ratio of from 1:0.01 to 1:1, preferably from 1:0.08 to 1:0.4, more preferably from 1:0.15 to 1:0.25, in the mixture of the starting compounds. The two chelating oxo ligands can each have the same Mo/oxo ligand ratio or a different ratio.

The synthesis according to the invention not only gives an MoVTeNb mixed oxide having a high phase purity in respect of the M1 phase, but the MoVTeNb mixed oxide obtained also represents a catalyst material having an improved activity in the oxidation of ethane to ethylene. A further advantage of the synthesis according to the invention of the M1 phase is the high efficiency of the conversion of the starting materials by means of the hydrothermal synthesis.

If the stoichiometry of the starting materials is in the range Mo/V/Nb/Te=1:0.22:0.1:0.1 to 1:0.3:0.17:0.17, Mo, V, Nb and Te are converted virtually completely into the M1 phase, so that less than 100 ppm of all metals remains in the mother liquor. The possible stoichiometry of the M1 phase is adequately known from the literature and can be expressed by the formula $Mo/V_aNb/Te_cO_x$ where a=0.2 to 0.3, b=0.1 to 0.2, c=0.1 to 0.25 and x being a variable which leads, as a function of the oxidation state of the metals (Mo, V, Nb and Te), to charge balance.

In addition, it has been found that when $MoO_3$, $V_2O_5$, $Nb_2O_5$ and $TeO_2$ are used together with citric acid, glycol and oxalic acid, the hydrothermal crystallization occurs highly successfully. The crystallization is particularly successful in the absence of ammonium ions. Preference is therefore given to ammonium ions being absent in the synthesis.

The process of the invention gives a mixed oxide material comprising the elements molybdenum, vanadium, niobium and tellurium for the oxidation of ethane, which has the following stoichiometry:

$$Mo_1V_aNb_bTe_cO_x$$

where $0.27<a<0.31$; $0.08<b<0.12$; $0.08<c<0.12$, and which in the XRD has diffraction reflections h, i, k and l whose peaks are approximately at the diffraction angles (2θ) 26.2°±0.5° (h), 27.0°±0.5° (i), 7.8°±0.5° (k) and 28.0°±0.5° (l).

The MoVTeNb mixed oxide of the invention can be used as catalyst material for the oxidation and/or oxidative dehydrogenation ("ODH") of hydrocarbons, in particular for the oxidative dehydrogenation of ethane to ethylene. It can have a BET surface area of from 5 to 25 m²/g, particularly preferably from 5 to 15 m²/g.

The MoVTeNb mixed oxide produced by the process of the invention can be used as catalyst or catalyst material. It can be used in various ways in a commercial catalyst. For example, it can be processed by tableting to give catalyst pellets which can then be introduced into a reactor.

The catalyst material can also be processed together with a suitable binder to give an extrudate (pellets, shaped bodies, honeycomb bodies and the like). As binder, it is possible to use any binder material with which a person skilled in the art is familiar and which appears suitable. Preferred binders are, inter alia, pseudoboehmite and also siliceous binders such as colloidal silicon oxide or silica sol.

The catalyst material can also be processed together with other components, preferably with a binder, particularly preferably with an organic binder, for example an organic adhesive, polymers, resins or waxes, to give a washcoat which can be applied to a metallic or ceramic support. Additional impregnation steps or calcination steps can optionally be carried out.

The X-ray diffraction pattern of the MoVTeNb mixed oxide formed in the process of the invention has, when using Cu-Kα radiation, diffraction reflections h, i, k and l whose peaks are approximately at the diffraction angles (2θ) 26.2°±0.5° (h), 27.0°±0.5° (i), 7.8°±0.5° (k) and 28.0°±0.5° (l), where the intensities $P_h$, $P_i$, $P_k$, $P_l$ of the diffraction reflections h, i, k and l can satisfy the following relationships, where $R_x$ (x=1 to 3) is the intensity ratio defined by the relationships:

$R_1=P_h/(P_h+P_i)>0.3$, preferably >0.35 and particularly preferably >0.4; and/or $R_2=P_i/(P_i+P_l)>0.5$, preferably >0.6 and particularly preferably >0.63; and/or $R_3=P_i/(P_i+P_k)<0.8$, preferably <0.75 particularly preferably <0.7.

In the X-ray diffraction pattern (XRD) of embodiments of the mixed oxide material, the diffraction reflection i can have the second highest intensity and/or the diffraction reflection h can have the third highest intensity.

The MoVNbTe mixed oxide of the invention is used as catalyst material in the examples and will therefore sometimes be referred to as catalyst in the experimental part.

Figure 7:
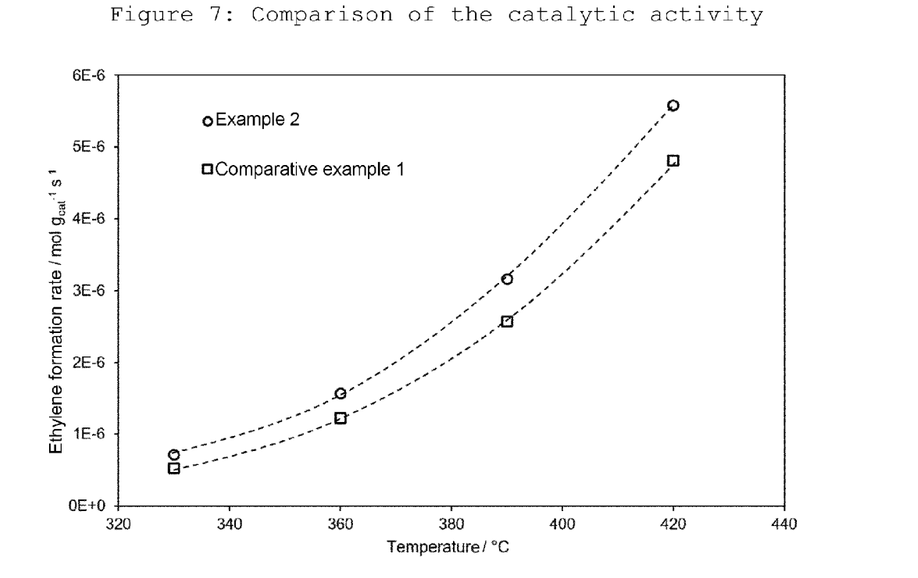
FIG. 7: comparison of the catalytic activity of the MoVTeNb mixed oxides of example 2 and comparative example 1 in the ODH of ethane.

The MoVTeNb mixed oxide produced by the novel process according to the invention is clearly more active. It achieves, normalized to 1 g of catalyst, a higher activity than the catalyst according to the prior art as per the comparative example (FIG. 7). This demonstrates that a mixed oxide material having new properties is obtained by the process of the invention. However, the new properties of the novel mixed oxide material cannot readily be measured using conventional characterization methods.

Methods of Characterization:

To determine the parameters of the catalysts according to the invention, the following methods are used:

1. BET Surface Area

The determination is carried out by the BET method of DIN 66131; a publication of the BET method may also be found in J. Am. Chem. Soc. 60, 309 (1938). The measurements were carried out at 77 K on a Sorptomatic 1990 instrument. The sample was evacuated for 2 hours at 523 K before the measurement. The linear regression of the isotherms according to the BET method was carried out in a pressure range of $p/p_0=0.01-0.3$ ($P_0=730$ torr).

2. X-Ray Powder Diffraction (XRD)

The X-ray diffraction patterns were recorded on a PANalytical Empyrean, equipped with a Medipix PIXcel 3D detector, in θ-θ geometry in an angle range of 2θ=5–70°. The X-ray tube produced Cu—K radiation. The Cu-Kβ radiation was suppressed by use of an Ni filter in the beam path of the incident X-ray beam, so that only Cu-Kα radiation having a wavelength of 15.4 nm (E=8.04778 keV) was diffracted by the sample.

The height of the source-side beam path was adapted by means of an automatic divergence slit (programmable divergence slit—PDS) in such a way that the sample was irradiated over a length of 12 mm over the entire angle range. The width of the detector-side X-ray beam was restricted to 10 mm by means of a fixed orifice plate. Horizontal divergence was minimized by use of a 0.4 rad Soller slit.

The height of the detector-side beam path was adapted in a manner analogous to the source-side beam path by means of an automatic anti-scatter slit (programmable anti-scatter slit—PASS) in such a way that the X-ray beam reflected by the sample over a length of 12 mm was detected over the entire angle range.

The samples, depending on the amount available, were prepared either on an amorphous silicon sample plate or tableted as flat-bed samples.

3. Pore Distribution

The pore size distribution was measured by means of nitrogen sorption measurements at 77 K on a Sorptomatic instrument or a TriStar 3000 instrument. Before the measurement, the sample was evacuated for 2 h at 523 K. Both adsorption and desorption isotherms were determined and employed for the evaluation by the Barrett-Joyner-Halenda method (BJH).

The invention will now be illustrated with the aid of the following working examples, which are not to be construed as a restriction.

WORKING EXAMPLES

Example 1

$TeO_2$ (Alfa Aesar) was slurried in 200 g of distilled $H_2O$ and milled in a planetary ball mill using 1 cm balls ($ZrO_2$). The portion was subsequently transferred with the aid of 500 ml of distilled $H_2O$ into a glass beaker. The $Nb_2O_5$ was slurried in 200 g of distilled $H_2O$ and milled in the same ball mill. The portion was subsequently transferred with the aid of 500 ml of distilled $H_2O$ into a glass beaker. On the next morning the $Nb_2O_5$ suspension was heated to 80° C. and 107.8 g of oxalic acid dihydrate were added and the mixture was stirred for about 1 hour. 6 l of distilled $H_2O$ were placed in an autoclave (40 l) and heated to 80° C. while stirring (speed of the stirrer: 90 rpm). When the water had reached this temperature, 61.58 g of citric acid, 19.9 g of ethylene glycol, 615.5 g of $MoO_3$ (Sigma Aldrich), 124.5 g of $V_2O_5$, the milled $TeO_2$ and the milled $Nb_2O_5$ in oxalic acid were added in succession. 850 ml of distilled $H_2O$ were used for transferring and rinsing the vessels. The total amount of water in the autoclave is 8.25 l. The contents of the autoclave were subsequently blanketed with nitrogen. A hydrothermal synthesis at 190° C./48 hours was carried out in the 40 l autoclave. After the synthesis, the mixture was filtered on a blue band filter with the aid of a vacuum pump and the filter cake was washed with 5 l of distilled $H_2O$.

Drying was carried out at 80° C. for 3 days in a drying oven and the product was subsequently milled in an impact mill. A solids yield of 0.8 kg was achieved.

The subsequent calcination was carried out at 280° C. for 4 hours in air (heating rate 5° C./min, air: 1 l/min).

Activation was carried out in a retort at 600° C. for 2 hours (heating rate 5° C./min, $N_2$: 0.5 l/min).

The product had a BET surface area of 9 $m^2/g$ and a pore volume=0.04 $cm^3/g$.

Example 2

75 ml of twice-distilled water were placed in a 100 ml PTFE beaker, 177.8 mg of (mono)ethylene glycol were added dropwise and 5397.9 mg of $MoO_3$, 1023.9 mg of $V_2O_5$, 599.1 mg of $TeO_2$, 549.5 mg of $Nb_2O_5 \cdot xH_2O$ (Nb=63.45% by weight), 540.9 mg of citric acid and 338.3 mg of oxalic acid were subsequently slurried in. The Teflon beaker was closed and transferred into a stainless steel autoclave bomb. This was closed in a pressure-tight manner and clamped onto a horizontally rotating shaft in an oven which had been preheated to 190° C. After 48 hours, the autoclave bomb was taken from the oven and immediately quenched under running water and subsequently cooled in an ice bath for 45 minutes.

The product suspension formed was filtered through filter paper (pore width 3 μm) and the solid was washed with 200 ml of twice-distilled water.

The product obtained in this way was dried at 80° C. for 16 hours in a drying oven and then ground in a hand mortar.

Figure 1:
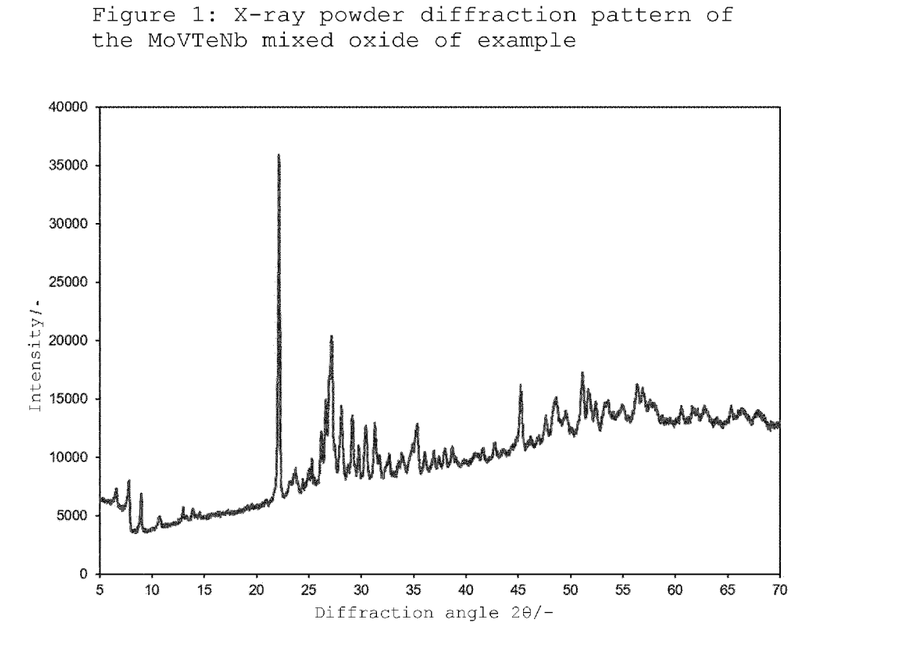
FIG. 1: XRD of the MoVTeNb mixed oxide of example 1.
Figure 2:
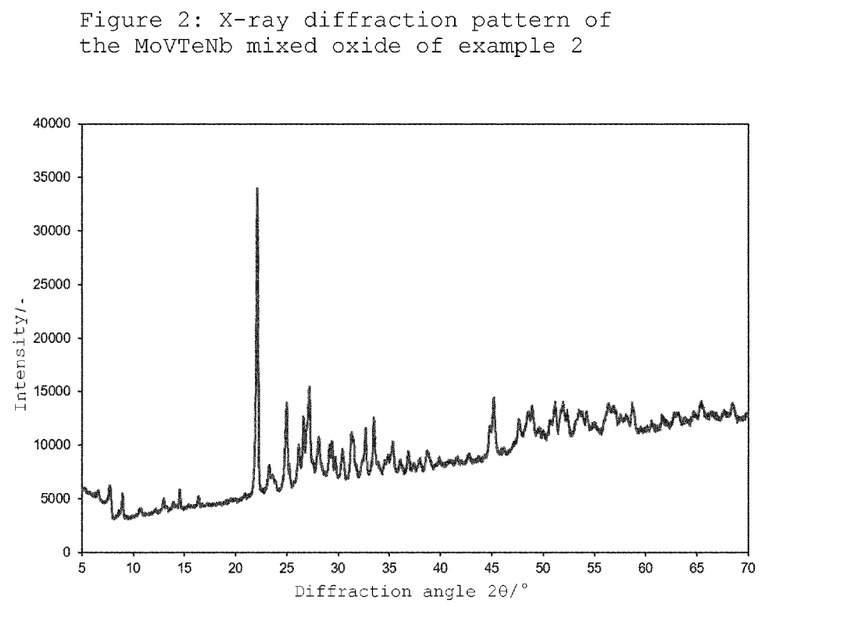
FIG. 2: XRD of the MoVTeNb mixed oxide of example 2.
Figure 3:
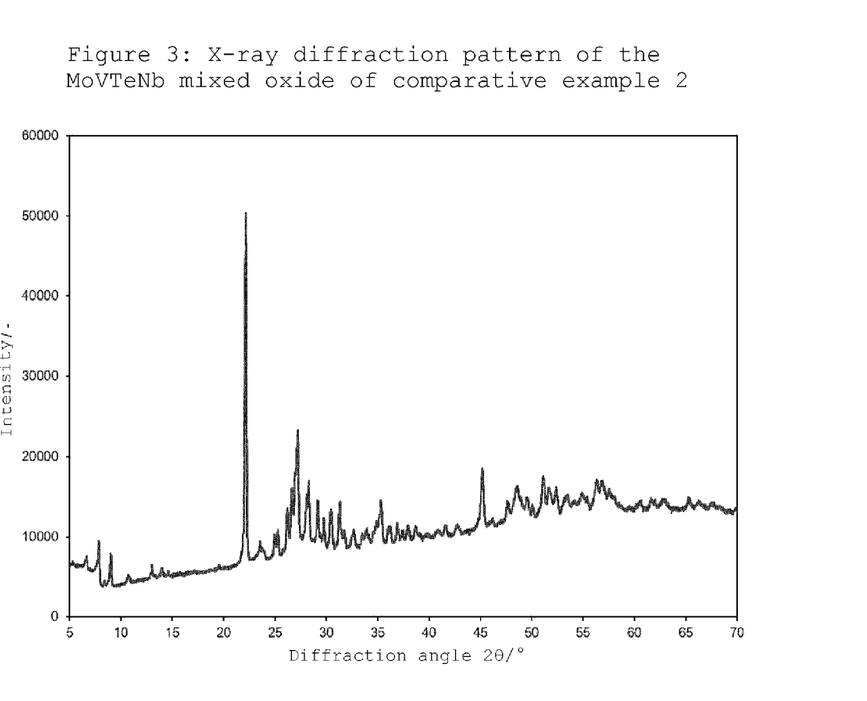
FIG. 3: XRD of the MoVTeNb mixed oxide of comparative example 1.
Figure 4:
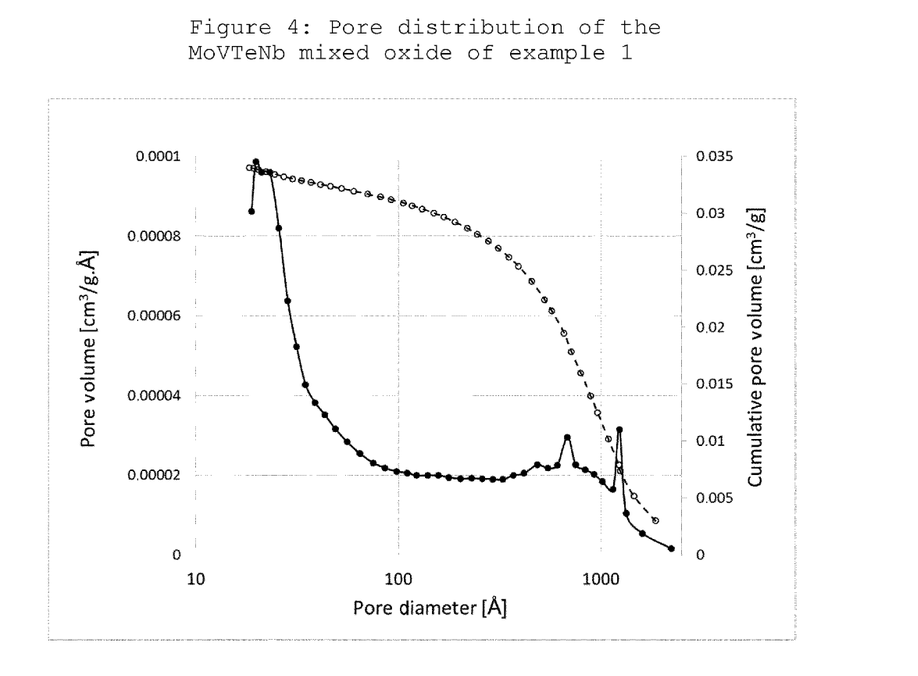
FIG. 4: Pore distribution of the MoVTeNb mixed oxide of example 1.
Figure 5:
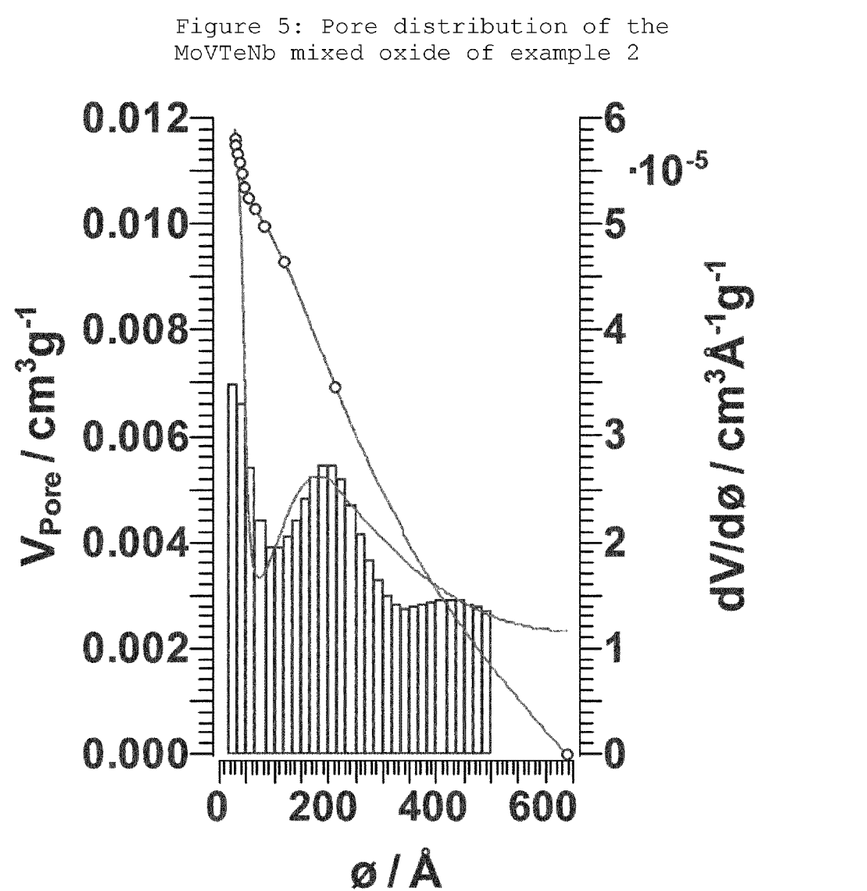
FIG. 5: Pore distribution of the MoVTeNb mixed oxide of example 2.
Figure 6:
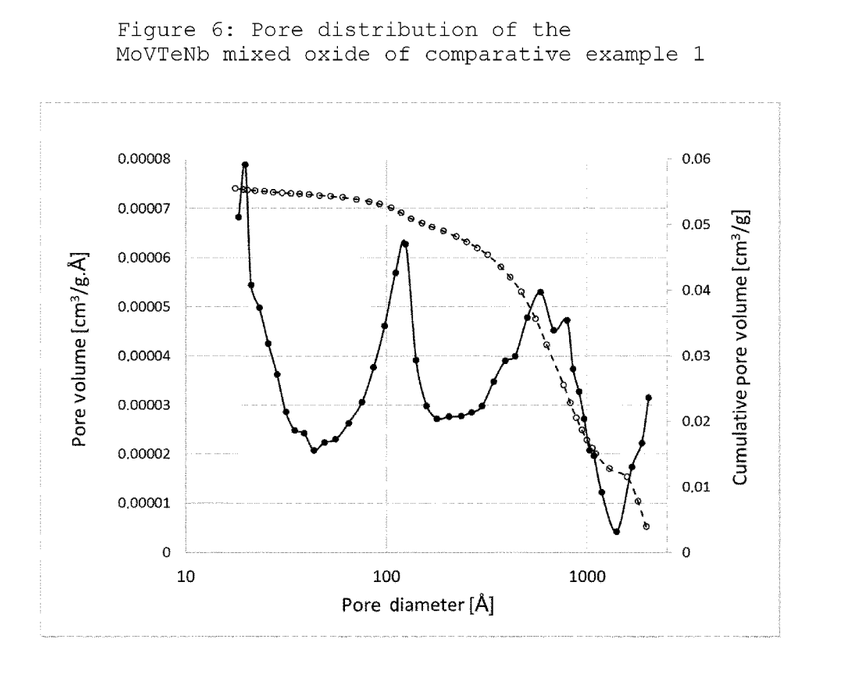
FIG. 6: Pore distribution of the MoVTeNb mixed oxide of comparative example 1.

The solids yield was 6.2 g. The activation was carried out at 600° C. for 2 hours (heating rate 10° C./min, $N_2$: 100 ml/min). The XRD diffraction pattern of the product is shown in FIG. 2, the BET surface area was 7.3 $m^2/g$ and the pore volume was less than 0.012 $cm^3/g$.

Comparative Example 1

3.3 l of distilled $H_2O$ are placed in an autoclave (40 l) and heated to 80° C. while stirring. Meanwhile, 725.58 g of ammonium heptamolybdate tetrahydrate (from HC Starck) were introduced and dissolved (AHM solution). In each of three 5 l glass beakers, 1.65 l of distilled $H_2O$ were likewise heated to 80° C. while stirring on a magnetic stirrer with temperature regulation. 405.10 g of vanadyl sulfate hydrate (GfE, V content: 21.2%), 185.59 g of ammonium niobium oxalate (HC Starck, Nb content: 20.6%) and 94.14 g of telluric acid, respectively, were then introduced into these glass beakers and dissolved (V solution, Nb solution and Te solution).

The V solution, the Te solution and finally the Nb solution were then pumped by means of a peristaltic pump into the AHM solution; pumping time: V solution: 4.5 min at 190 rpm (tube diameter: 8×5 mm), Nb solution: 6 min at 130 rpm (tube diameter: 8×5 mm).

The suspension formed was stirred further at 80° C. for 10 minutes. The speed of the stirrer during the precipitation was 90 rpm.

The suspension was subsequently blanketed with nitrogen by building up a pressure up to about 6 bar in the autoclave by means of nitrogen and opening the discharge valve to such an extent that flow under a pressure of $N_2$ occurred through the autoclave (5 minutes). At the end, the pressure was released again to a residual pressure of 1 bar via the venting valve.

The hydrothermal synthesis was carried out at 175° C. for 20 hours (heating time: 3 hours) in the 40 l autoclave using an anchor stirrer at a stirrer speed of 90 rpm.

After the synthesis, the suspension was filtered on a blue band filter by means of a vacuum pump and the filter cake was washed with 5 l of distilled $H_2O$.

Drying was carried out at 80° C. for 3 days in a drying oven and the solid was subsequently milled in an impact mill; the solids yield was 0.8 kg.

Calcination was carried out at 280° C. for 4 hours (heating rate of 5° C./min, air: 1 l/min). Activation was carried out at 600° C. for 2 hours in the retort (heating rate 5° C./min, $N_2$: 0.5 l/min).

The BET surface area of the product was 9 $m^2/g$, and the pore volume=0.055 $cm^3/g$.

Example 3

The catalytic activity of the catalysts of example 2 and the comparative example in the oxidative dehydrogenation of ethane was examined in a tubular reactor under atmospheric pressure in the temperature range from 330 to 420° C. For this purpose, 25 mg (example 2) or 200 mg (comparative example 1) of catalyst (particle size from 150 to 212 μm) were diluted with silicon carbide (particle size from 150 to 212 μm) in a mass ratio of 1:5. A layer of 250 mg of silicon carbide of the same particle size was introduced both below and above the catalyst bed and the ends of the tube reactor were closed by means of quartz wool plugs.

The reactor was flushed with inert gas before commencement of the experiment and subsequently heated to 330° C. under a helium flow of 50 sccm. After the desired temperature had been reached and was stable for one hour, the gas fed in was switched over to the reaction gas mixture.

The inlet gas composition was $C_2H_6/O_2/He=9.1/9.1/81.8$ (v/v) at a total volume flow of 50 sccm.

Analysis of the product gas stream was carried out in a gas chromatograph equipped with Haysep N and Haysep Q columns, a 5 A molecular sieve column and a thermal conductivity detector.

The ethylene formation rates under the above-described conditions are shown in FIG. 7.

The invention claimed is:

1. A process for producing a mixed oxide material, comprising the steps:
   a) production of a mixture of starting compounds, which contains starting compounds comprising molybdenum, vanadium, niobium, and tellurium, and also contains oxalic acid, a first chelating oxo ligand, and a second chelating oxo ligand,
   b) hydrothermal treatment of the mixture of starting compounds at a temperature of from 100° C. to 300° C. to give a product suspension,
   c) isolation and drying of the solid present in the product suspension resulting from step b), and
   d) activation of the solid obtained from step c) in an inert gas,
wherein the mixture of starting compounds contains
   tellurium dioxide or a compound of the formula $M_x^{n+}TeO_3$ where n=1 or 2 and x=2/n, where M is an alkali metal or alkaline earth metal, and
   at least one of molybdenum trioxide, vanadium pentoxide, and niobium pentoxide.

2. The process as claimed in claim 1, wherein the activation in step d) is carried out at a temperature in the range from 450° C. to 700° C.

3. The process as claimed in claim 1, wherein the mixture of starting compounds contains molybdenum trioxide.

4. The process as claimed in claim 1, wherein the mixture of starting compounds contains vanadium pentoxide.

5. The process as claimed in claim 1, wherein the mixture of starting compounds contains niobium pentoxide.

6. The process as claimed in claim 5, wherein the niobium pentoxide has a particle size $D_{90}$ of less than 100 μm.

7. The process as claimed in claim 1, wherein the mixture of starting compounds contains tellurium dioxide having a particle size $D_{90}$ of less than 100 μm.

8. The process as claimed in claim 1, wherein the first chelating oxo ligand or the second chelating oxo ligand is ethylene glycol, present in a molar ratio to molybdenum of 0.01:1 to 1:1.

9. The process as claimed in claim 1, wherein the first chelating oxo ligand or the second chelating oxo ligand is citric acid.

10. A mixed oxide material for the oxidation of ethane, which comprises the elements molybdenum, vanadium, niobium and tellurium and has the following stoichiometry:

$$Mo_1V_aNb_bTe_cO_x$$

where 0.27<a<0.31; 0.08<b<0.12; 0.08<c<0.12,
and which in the XRD, when using Cu-Kα radiation, has diffraction reflections h, i, k and l whose peaks are approximately at the diffraction angles (2θ) 26.2°±0.5° (h), 27.0°±0.5° (i), 7.8°±0.5° (k) and 28.0°±0.5° (l).

11. The use of the mixed oxide material as claimed in claim 10 for the oxidative dehydrogenation of ethane to ethene.

12. The use of the mixed oxide material as claimed in claim 10 for the oxidation of propane.

13. The process as claimed in claim 1, wherein each chelating oxo ligand is independently present in the mixture of starting compounds in a molar ratio to molybdenum of 0.08:1 to 0.4:1.

14. The process as claimed in claim 1, wherein the product suspension resulting from step b) includes the mixed oxide material, having the following stoichiometry:

$$Mo_1V_aNb_bTe_cO_x$$

where 0.27<a<0.31; 0.08<b<0.12; 0.08<c<0.12,
and which in the XRD, when using Cu-Kα radiation, has diffraction reflections h, i, k and l whose peaks are approximately at the diffraction angles (2θ) 26.2°±0.5° (h), 27.0°±0.5° (i), 7.8°±0.5° (k) and 28.0°±0.5° (l).

15. The process as claimed in claim 1, wherein the product suspension resulting from step b) comprises a mother liquor including less than 100 ppm of a combined amount of molybdenum, vanadium, niobium, and tellurium.

16. The process as claimed in claim 1, wherein each chelating oxo ligand is independently present in the mixture of starting compounds in a molar ratio to molybdenum of 0.08:1 to 0.4:1.

17. A process for producing a mixed oxide material, comprising the steps:
   a) production of a mixture of starting compounds, which contains starting compounds comprising molybdenum, vanadium, niobium, and tellurium, and also contains oxalic acid a first chelating oxo ligand and a second chelating oxo ligand, wherein molybdenum is present in the mixture
      in an atomic ratio to vanadium of 1:0.22 to 1:0.3,
      in an atomic ratio to niobium of 1:0.1 to 1:0.17, and
      in an atomic ratio to tellurium of 1:0.1 to 1:0.17,
   b) hydrothermal treatment of the mixture of starting compounds at a temperature of from 100° C. to 300° C. to give a product suspension,
   c) isolation and drying of the solid present in the product suspension resulting from step b), and
   d) activation of the solid obtained from step c) in an inert gas,
wherein the mixture contains tellurium dioxide or a compound of the formula $M_x^{n+}TeO_3$ where n=1 or 2 and x=2/n, where M is an alkali metal or alkaline earth metal.

18. The process as claimed in claim 17, wherein the mixture of starting compounds includes at least one of molybdenum trioxide, vanadium pentoxide, and niobium pentoxide.

19. The process as claimed in claim 17, wherein the product suspension resulting from step b) includes the mixed oxide material, having the following stoichiometry:

$$Mo_1V_aNb_bTe_cO_x$$

where 0.27<a<0.31; 0.08<b<0.12; 0.08<c<0.12,
and which in the XRD, when using Cu-Kα radiation, has diffraction reflections h, i, k and l whose peaks are approximately at the diffraction angles (2θ) 26.2°±0.5° (h), 27.0°±0.5° (i), 7.8°±0.5° (k) and 28.0°±0.5° (l).

20. The process as claimed in claim 17, wherein the product suspension resulting from step b) comprises a mother liquor including less than 100 ppm of a combined amount of molybdenum, vanadium, niobium, and tellurium.

* * * * *